United States Patent [19]

McDougall

[11] Patent Number: 5,435,032
[45] Date of Patent: Jul. 25, 1995

[54] TOOTHBRUSH

[75] Inventor: Gregory J. McDougall, Kowloon, Hong Kong

[73] Assignee: ISIS International, Inc., Tortola, Virgin Islands (Br.)

[21] Appl. No.: 185,850
[22] PCT Filed: May 25, 1993
[86] PCT No.: PCT/GB93/01069
§ 371 Date: Mar. 17, 1994
§ 102(e) Date: Mar. 17, 1994
[87] PCT Pub. No.: WO93/24034
PCT Pub. Date: Dec. 9, 1993

[30] Foreign Application Priority Data
May 28, 1992 [GB] United Kingdom ............... 9211338

[51] Int. Cl.$^6$ ............................................. A61C 17/34
[52] U.S. Cl. ......................................... 15/22.1; 15/201
[58] Field of Search ................. 15/22.1, 22.2, 22.4, 15/201, 203, 167.1

[56] References Cited

U.S. PATENT DOCUMENTS 4,545,087 10/1985 Nahum ............................ 15/22.1

FOREIGN PATENT DOCUMENTS 1166163 6/1958 France ............................ 15/22.1

Primary Examiner—Edward L. Roberts, Jr.
Attorney, Agent, or Firm—Omri M. Behr; Matthew J. McDonald

[57] ABSTRACT

A toothbrush head consists of a hollow body (16) closed at one side by a flexible membrane (13) formed with cavities (17) to hold bases of tufts of bristles. The cavities form protrusions extending up inside the body (16) which are pushed against by a reciprocating finger (18) to tilt and move the bristles relative to the body (16).

7 Claims, 3 Drawing Sheets

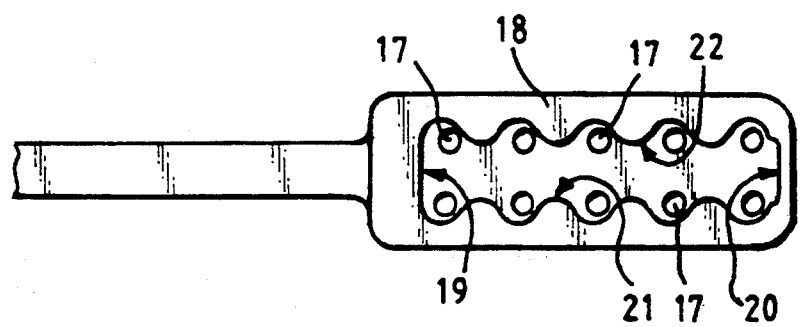
FIG.5
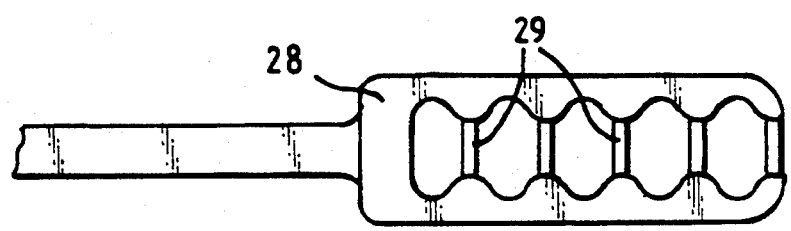
FIG.6
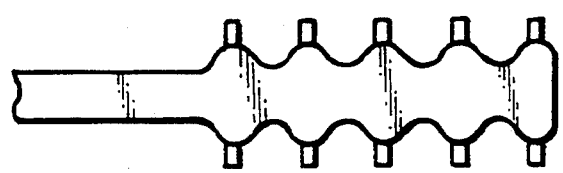 
FIG.7          FIG.7A
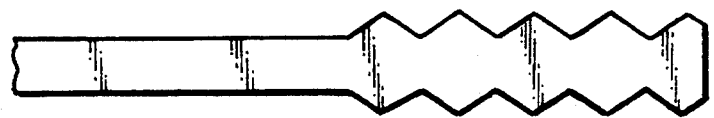
FIG.8

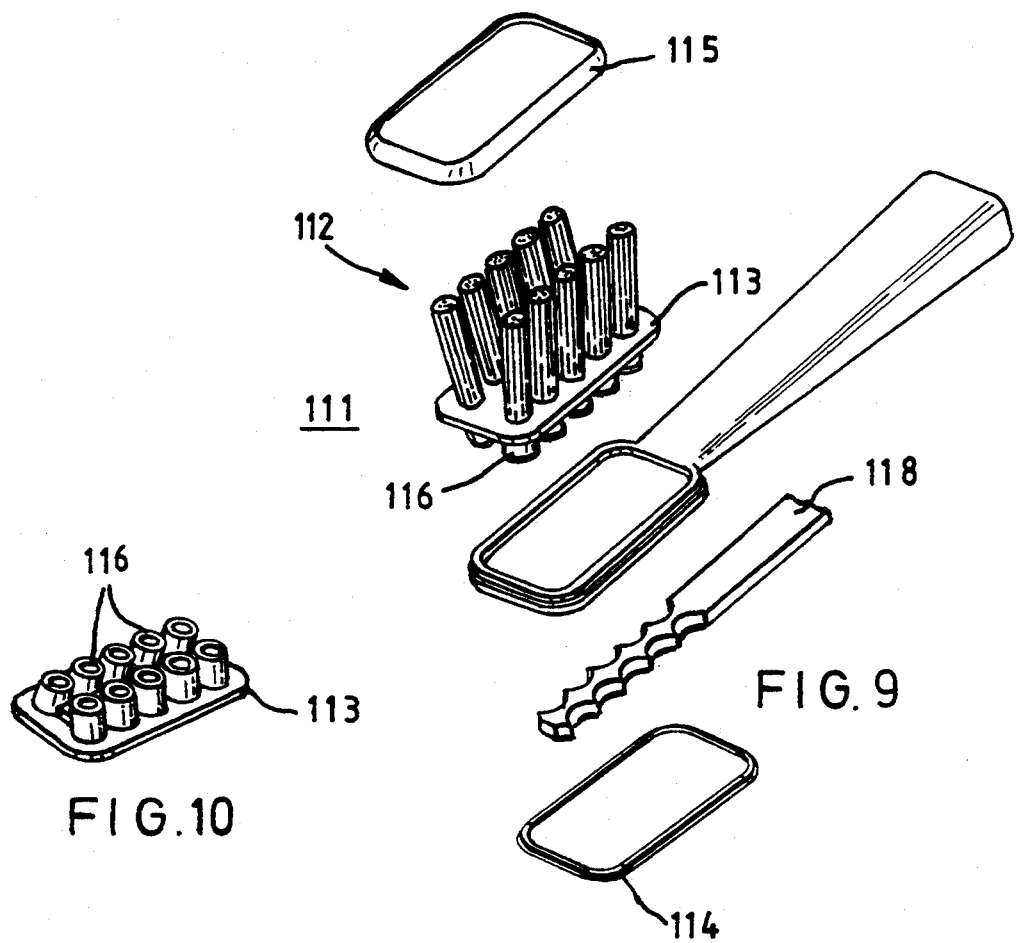
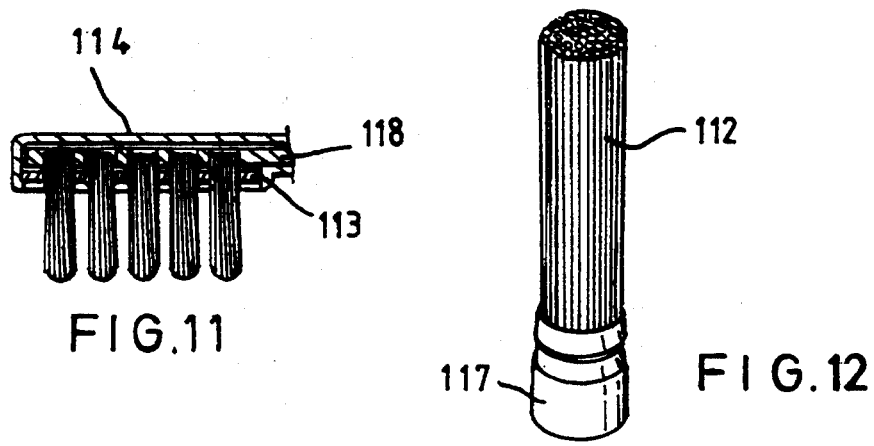

TOOTHBRUSH

The invention relates to toothbrushes.

The invention relates more particularly to electrically driven toothbrushes in which brush bristles are arranged to be moved relative to the brush holder.

There are many examples of such toothbrushes including the disclosure in 1939 of rotary driven bristles in U.S. Pat. No. 2,215,031. A similar rotational drive arrangement is also shown in U.S. Pat. No. 4,845,795. U.S. Pat. No. 4,156,620 explains how a rotational motor drive is converted into reciprocal linear motion to drive the bristles rotationally clockwise and counterclockwise. U.S. Pat. No. 3,577,579 discloses a toothbrush in which a toothbrush head is moved in relation to a brush holder so that all the bristles mounted in the brush head move together sideways and backwards and forwards relative to the holder.

The last mentioned arrangement is not very satisfactory for cleaning teeth and especial gingivial regions and the other prior art arrangements suffer from being mechanically complex and liable to ingress of water and other contamination.

It is an object of the invention to overcome or at least reduce the disadvantages of the prior art arrangements.

According to the invention there is provided a tooth brush head comprising a hollow body closed at one side by a resilient material membrane extending over the one side and formed with an array of cavities to receive and hold bases of tufts of bristles the ends of which extend away from the body at the one side, in which the walls of the cavities enclosing the bases extend into the hollow body having or thereby forming protrusions, and at least one movable finger extending along inside the body which is arranged to be driven in use to push against and move respective of the cavities or protrusions and hence move the ends of the bristles relative to the hollow body in accordance therewith.

The finger may be arranged to be driven backwards and forwards along the inside of the body.

The finger may be arranged alternatively or additionally to push each respective protrusion in one or more directions a right angles to the longitudinal axes of the bristles.

The finger may also be arranged to push the protrusions parallel to the longitudinal axes of the bristles.

A tooth brush heads according to the invention will now be described by way of example with reference to the accompanying drawings in which:

FIG. 5 is a diagramatic view of the inside of part of the head;

FIG. 6 is a diagramatic view of the inside of part of a modified head;

FIG. 7 is a diagramatic view of the inside of part of a different head;

FIG. 7A is an end view of FIG. 7;

FIG. 8 is a diagramatic view of the inside of a part of a further head.

FIG. 9 is an exploded isometric view of a different head;

FIG. 10 is an isometric view of a resilient membrane for the head of FIG. 9;

FIG. 11 is a sectional side view of part of the head of FIG. 9; and

FIG. 12 is an enlarged view of a tuft for use with the head of FIG. 9.

Figure 1:
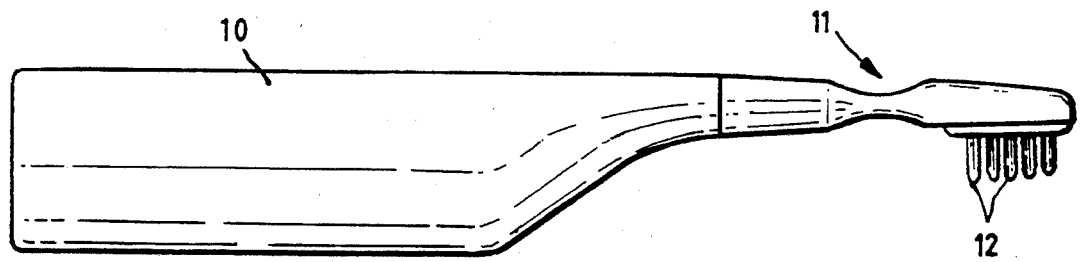
FIG. 1 is a side view of a toothbrush.

Referring to the drawings, in FIG. 1 a battery operated toothbrush has a handle 10 and a head 11. The arrangement of the handle is well-known and contains a battery and motor which drives a gear to convert the rotary motor drive into reciprocating motion, such an arrangement is shown for example in U.S. Pat. No. 4,156,620 but many other drive arrangements are known. Embodiment of the invention relate basically to the arrangement of heads and not to the motor and drive mechanisms and so no further description of the motor and drive mechanisms will be provided in this specification.

Figure 2:
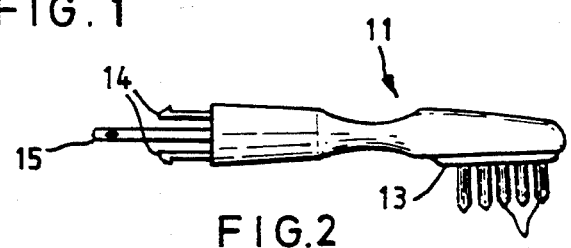
FIG. 2 is a side view of a toothbrush head.

In FIG. 2, the head 11 is shown with tufts 12 of bristles, of generally conventional type, fixed and securely held in a resilient membrane 13. A snap-on connector 14 is provided to releasable attach and hold the head 11 to the handle 10. One end 15, of a finger to be described below, extends out of the handle 10 for attachment to the head 11 and is activated by a drive mechanism inside the handle 10. When the head is attached to the handle 10 the mechanism moves the finger backwards and forwards inside the head 11 when the motor is switched on.

Figure 3:
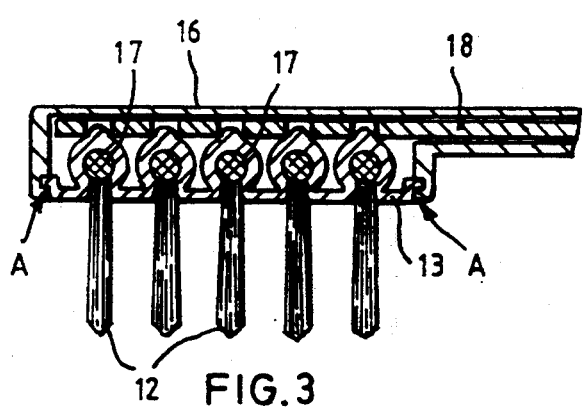
FIG. 3 is a cross-sectional side view of part of the head.

In FIG. 3, the head 11 consists of a hollow body 16 having one side closed by the membrane 13 which is formed with an array of cavities 17 which surround and securely hold bases of the tufts 12. The bases may be arranged to spring in and out of the cavities 17 so that tufts of bristles may be changed or replaced for different applications or when the bristles become worn in use. The membrane 13 extends across the one side of the body 16 and is sealed around its peripheral edge, as seen for example at A, to prevent any moisture or other contamination entering the body 16. The cavities 17 are integrally formed in the membrane and close around the bases of the tufts as shown to form protrusions extending up inside the body 16. The finger 18, which extends from the handle to the end 15 in FIG. 2, is positioned along and inside the body 16 to press in use against outer closed surfaces of the cavities 17 when the finger 18 is moved backwards and forwards to provide in use movement of those cavity surfaces and hence the extreme ends of the bristles as described below.

In FIG. 5, the finger 18 is shown in nearly one extreme position, its position nearly fully to the right in respect of the drawing, and in use the finger is moved so that its inner end surfaces 19 and 20 press the end cavities 17 somewhat to the right and somewhat to the left respectively at the extreme ends of backward and forward movement of the finger 18. The inner side surfaces 21 and 22 of the finger 18 are sinuosoidal and such that when the finger 18 moves backwards and forwards the cavities 17 are moved respectively up and down, in respect to the drawing. The movement of the cavities 17 provides the necessary and desirable movement of the brush bristles against the teeth and into the gingivial regions when the toothbrush is used in otherwise normal fashion.

Figure 3A:
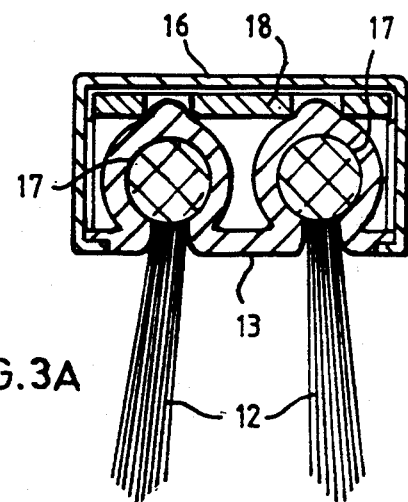
FIG. 3A is an enlarged cross-sectional end view of part of the head.
Figure 4:
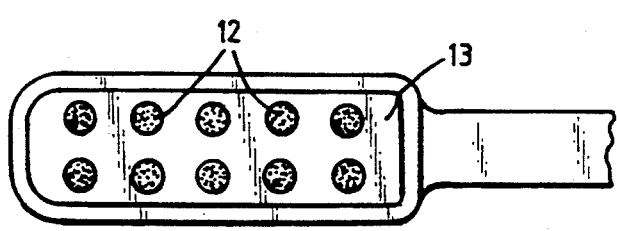
FIG. 4 is an underside view of the head.

It will be appreciated that the action of the sinuosidal shape of the surfaces 21 and 22 against the cavities actually causes the extreme ends of the bristles to move not only left and right relative to the longitudinal axis of the finger 18 by also to some extent through a circular or part-circular path. That is because the sinusoidal surfaces not only push the cavities to the left or right but also to some extent to the front and the back (i.e. parallel to the longitudinal axis of the finger 18). In fact by differently shaping the finger surfaces, which in use contact and push the outer surfaces of the cavities, many different patterns of movement for the extreme ends of the brushes can be achieved. The degree of movement is not only dependent on the shape of these surfaces but is also dependent on the height that finger is constrained to move in the body 16, relative to the central points of the base of the tufts (see FIG. 3A for example where the bristles are tilted away from another at their extreme ends). Generally, the tufts will tend to pivot naturally about geometric centres of their respective bases and the more off-set from these axes that the longitudinal plane of the finger is arranged, the more the ends of the bristles can, in general terms, be arranged to move relative to the head 11.

In this respect, it is also possible to form the cavities with or provide upward extensions attached thereto to provide protrusions against which the finger 18 presses. Such upward extensions enable the finger to be higher up inside the body (which body would be deeper to accommodate the finger) and of course enable the "protrusions" to have a smaller cross-section where they are contacted by the finger, the finger of FIG. 5 may thus be smaller in cross-section as well. More importantly, the movement caused by the finger 18 pressing against extended protrusions can have a better mechanical advantage to pivot, in effect, the cavity more and so move the extreme ends of the bristles about a wide cross-sectional path where desirable.

In FIG. 6, the finger 28 is generally the same shape as the finger 18 of FIG. 5. The finger 28 has additionally cross bars 29 which are arranged to press down against the top outer surfaces of the cavities 17 or protrusions. Thus, as the finger 28 moves backwards and forwards, it causes the cavities to move to the left and to the right, and to some extent backwards and forwards as explained above. The finger 28 also moves the cavities and thus the extreme ends of the bristles up and down in relation to the head 11.

Other shapes of finger 18 are shown in FIGS. 7 and 8.

The finger in the described embodiments moves backwards and forwards but a rotary finger could be used, formed with eccentric cams or the like, to bear against and move the protrusions from side to side and/or backwards and forwards in a similar manner as before.

Referring to FIGS. 9 to 12, the different head 111 has an array of tufts 112 held securely in use in a resilient membrane 113. The head 111 is closed by a lid 114 and has a retaining ring 115 which holds the membrane 113 to the head. The membrane provides an array of hollow upstanding protrusions 116 into which each one end of the tufts 112 fits inside a metallic or plastics end cap 117 (see FIG. 12). The tops of the end caps 117 close off and seal the upper ends of the protrusions 116. A finger 118 is provided for moving the tufts in the same manner as described earlier.

Normally, and as required in the tooth brush shown in FIG. 3, the finger 18 presses against the outer surfaces or top protrusions of the cavities 17, which cavities and protrusions are closed off and integrally formed with the membrane 13. It is possible with the arrangement shown in FIG. 9 that the caps 117 extend a little beyond the tops of the protrusions 116 to form additional protrusions. Then the finger 118 may be arranged to bear against the additional protrusions provided by the uppermost ends of the caps 117. In such an arrangement never-the-less seals off the user ends of the brushes are sealed off from inside of the head 111 where the finger 118 is located.

It is possible in embodiments of the invention for the finger to be arranged to push against only some of the protrusions and to have more than one finger in each hollow body. All embodiments of the invention in physically separating the bristles from the moving parts, indeed effectively sealing those parts from one another, ensure the user end of the bristles remain hygenic and can be easily washed and disinfected without damaging the moving parts. The resilient membrane is preferably formed as a moulded silicon rubber material. The desired movement for the bristles is transmitted while keeping the bristles and the driving arrangements totally sealed off from one another. Further, the contacting surfaces inside the hollow body of the head can be well-lubricated if desired without risk of the lubricant leaking from the head onto the user ends of the bristles.

I claim:

1. A tooth brush head comprising a hollow body closed at one side by a resilient material membrane extending over the one side and formed with an array of cavities to receive and hold bases of tufts of bristles the ends of which extend away from the body at the one side, in which the walls of the cavities enclosing the bases extend into the hollow body having or thereby forming protrusions, and at least one movable finger extending along inside the body which is arranged to be driven in use to push against and move respective of the cavities or protrusions and hence move the ends of the bristles relative to the hollow body in accordance therewith.

2. A tooth brush head according to claim 1, in which the walls of the cavities are integrally formed and each closed at one end.

3. A tooth brush head according to claim 1, in which the finger is arranged to be driven backwards and forwards along the inside of the body.

4. A tooth brush head according to claim 3, in which the finger is formed with an irregular surface which bears against the at least some of the protrusions to move the protrusions laterally with respect to the longitudinal axis of the finger when the finger moves backwards and forwards.

5. A tooth brush head according to claim 4, in which the surface is shaped to move the protrusions in addition partially or to some extent in a direction parallel to the longitudinal axis of the finger when the finger moves backwards and forwards.

6. A tooth brush head according to claim 1, in which the finger is arranged to push each respective protrusion in one or more directions at right angles to the longitudinal axes of the bristles.

7. A tooth brush head according to claim 1, in which the finger is arranged to push each respective protrusion in a direction parallel to the longitudinal axes of the bristles.

* * * * *